US00PP21004P2

(12) United States Plant Patent
Hooijman

(10) Patent No.: US PP21,004 P2
(45) Date of Patent: May 25, 2010

(54) ROSE PLANT NAMED 'ESM DURAZNO'

(50) Latin Name: *Rosa hybrida*
Varietal Denomination: Esm Durazno

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 0 days.

(21) Appl. No.: 12/319,412

(22) Filed: Jan. 7, 2009

(51) Int. Cl.
*A01H 5/00* (2006.01)

(52) U.S. Cl. ..... Plt./136

(58) Field of Classification Search ..... Plt./136, Plt./137
See application file for complete search history.

*Primary Examiner*—June Hwu
(74) *Attorney, Agent, or Firm*—C. A. Whealy

(57) ABSTRACT

A new and distinct cultivar of Rose plant named 'Esm Durazno', characterized by its long, strong and upright flowering stems; small durable foliage; freely and uniformly flowering habit; light salmon pink-colored flowers; and excellent postproduction longevity.

1 Drawing Sheet

Botanical designation: *Rosa hybrida.*
Cultivar denomination: 'ESM DURAZNO'.

BACKGROUND OF THE INVENTION

The present Invention relates to a new and distinct cultivar of Rose plant, botanically known as *Rosa hybrida*, commercially used as a cut flower Rose plant, and hereinafter referred to by the name 'Esm Durazno'.

The new Rose plant is a product of a planned breeding program conducted by the Inventor in El Quinche, Pichincha, Ecuador. The objective of the breeding program was to develop new freely-flowering cut flower Rose varieties with novel and attractive flower colors and excellent postproduction longevity.

The new Rose plant originated from a cross-pollination made by the Inventor in April, 2001 of a proprietary Rose selection identified as code number 92, not patented, as the female, or seed, parent with a proprietary Rose selection identified as code number 87, not patented, as the male, or pollen, parent. The new Rose plant was discovered and selected by the Inventor as a single flowering plant within the progeny of the stated cross-pollination in a controlled greenhouse environment in El Quinche, Pichincha, Ecuador in April, 2003.

Asexual reproduction of the new Rose plant by cuttings at El Quinche, Pichincha, Ecuador since August, 2003, has shown that the unique features of this new Rose plant are stable and reproduced true to type in successive generations of asexual reproduction.

SUMMARY OF THE INVENTION

The following traits have been repeatedly observed and are determined to be the unique characteristics of 'Esm Durazno'. These characteristics in combination distinguish 'Esm Durazno' as a new and distinct cultivar:

1. Long, strong and upright flowering stems.
2. Small durable foliage.
3. Freely and uniformly flowering habit.

4. Light salmon pink-colored flowers.
5. Excellent postproduction longevity.

Plants of the new Rose differ from plants of the female parent selection in the following characteristics:

1. Plants of the new Rose have fewer thorns than plants of the female parent selection.
2. Plants of the new Rose have larger flowers than plants of female parent selection.
3. Plants of the new Rose and the female parent selection differ in flower color as plants of the female parent selection have pink-colored flowers.

Plants of the new Rose differ from plants of the male parent selection in the following characteristics:

1. Plants of the new Rose are taller than plants of the male parent selection.
2. Plants of the new Rose have larger flowers than plants of male parent selection.
3. Plants of the new Rose and the male parent selection differ in flower color as plants of the male parent selection have white-colored flowers.

Plants of the new Rose can be compared to plants of Rose 'Ilse', not patented. In side-by-side comparisons conducted in El Quinche, Pichincha, Ecuador, plants of the new Rose differed from plants of 'Ilse' in the following characteristics:

1. Plants of the new Rose were not as broad as plants of 'Ilse'.
2. Plants of the new Rose had smaller leaves and leaflets than plants of 'Ilse'.
3. Plants of the new Rose had smaller flowers than plants of 'Ilse'.
4. Plants of the new Rose and 'Ilse' differed in flower color as plants of 'Ilse' had light orange-colored flowers.

BRIEF DESCRIPTION OF THE PHOTOGRAPHS

The accompanying colored photographs illustrate the overall appearance of the new Rose plant, showing the colors as true as it is reasonably possible to obtain in colored reproductions of this type. Colors in the photographs may differ slightly from the color values cited in the detailed botanical description which accurately describe the colors of the new Rose.

The photograph at the upper left of the sheet comprises a side perspective view of a typical flowering stem of 'Esm Durazno'.

The photograph at the lower left of the sheet is a close-up view of a typical flowering stem of 'Esm Durazno'.

The photograph at the top right of the sheet is a close-up view of a typical flower of 'Esm Durazno'.

The photographs at the lower right of the sheet are close-up views of the upper and lower surfaces of typical leaves of 'Esm Durazno'.

DETAILED BOTANICAL DESCRIPTION

Plants of the new Rose have not been observed under all possible environmental conditions. The phenotype may vary somewhat with variations in environment such as temperature and light intensity, without, however, any variance in genotype. The aforementioned photographs, following observations and measurements describe plants grown in El Quinche, Pichincha, Ecuador, in a polyethylene-covered greenhouse and under commercial production practices. Plants were pinched about 13.5 weeks after planting. Plants were about 18 months old when the photographs and description were taken. During the production of the plants, day temperatures ranged from about 16° C. to 30° C., night temperatures ranged from about 12° C. to 16° C. and light levels ranged from about 800 to 1,200 foot-candles. In the following description, color references are made to The Royal Horticultural Society Colour Chart, 2001 Edition, except where general terms of ordinary dictionary significance are used.

Botanical classification: *Rosa hybrida* 'Esm Durazno'.

Parentage:

*Female, or seed, parent*.—Proprietary seedling selection of *Rosa hybrida* identified as code number 92, not patented.

*Male, or pollen, parent*.—Proprietary seedling selection of *Rosa hybrida* identified as code number 87, not patented.

Propagation:

*Type*.—By cuttings.

*Time to initiate roots*.—About seven to ten days at 26° C. to 30° C.

*Time to produce a rooted young plant*.—About four to five weeks at 22° C. to 26° C.

*Root description*.—Fibrous, fine; close to N199C in color.

*Rooting habit*.—Freely branching; moderately dense.

Plant description:

*Plant form*.—Upright plant habit; long, strong and upright flowering stems.

*Growth habit*.—Moderately vigorous; freely basal branching habit; dense and bushy growth habit; about twelve flowering stems develop per year.

*Plant height*.—About 115 cm.

*Plant width* (*spread*).—About 45 cm.

*Lateral branches*.—Length: About 78 cm. Diameter: About 7 mm. Internode length: About 4 cm. Texture: Smooth, glabrous. Color: Close to 146A. Thorns: Density: Low. Shape: Triangular with sharp acuminate apices. Height: About 6 mm. Diameter, at base: About 5 mm. Color, immature: Close to 178C. Color, mature: Close to 165C.

Foliage description:

*Arrangement*.—Alternate; compound with typically seven leaflets per leaf.

*Leaf length*.—About 15 cm.

*Leaf width*.—About 9 cm.

*Terminal leaflet length*.—About 5 cm.

*Terminal leaflet width*.—About 3 cm.

*Lateral leaflet length*.—About 4 cm.

*Lateral leaflet width*.—About 3 cm.

*Leaflet shape*.—Ovate to oval.

*Leaflet apex*.—Acute.

*Leaflet base*.—Attenuate.

*Leaflet margin*.—Serrate.

*Leaflet texture, upper and lower surfaces*.—Smooth, glabrous.

*Leaflet venation pattern*.—Pinnate.

*Leaflet color*.—Developing leaflets, upper surface: Close to 146A; towards the margins, close to 187B. Developing leaflets, lower surface: Close to 146A; towards the margins, close to 148A. Fully expanded leaflets, upper surface: Close to 139A; venation, close to 146D. Fully expanded leaflets, lower surface: Close to 147B; venation, close to 146C.

*Petioles, leaves*.—Length: About 2.6 cm. Diameter: About 2 mm. Texture, upper and lower surfaces: Pubescent. Color, upper surface: Close to 146B. Color, lower surface: Close to 145C.

*Petioles, leaflets*.—Length: About 2 cm. Diameter: About 1.3 mm. Texture, upper and lower surfaces: Pubescent. Color, upper surface: Close to 146B. Color, lower surface: Close to 146C.

*Stipules*.—Quantity/arrangement/appearance: Two, adnate to the petiole, leafy. Length: About 2 cm. Width: About 2 mm. Shape: Roughly deltoid. Apex: Acuminate. Base: Truncate. Margin: Serrate, irregular. Texture, upper and lower surfaces: Smooth, glabrous. Venation pattern: Pinnate. Color, upper and lower surfaces: Close to 143A.

Flower description:

*Flower type and habit*.—Light pink-colored flowers; consistently symmetrical rosette flowers; freely flowering habit with about six flowers per terminal spray.

*Flowering season*.—Year-round under greenhouse conditions, optimal flowering from spring through autumn under garden conditions; flowering intermittent.

*Spray height*.—About 17.7 cm.

*Spray diameter*.—About 16.4 cm.

*Flower diameter*.—About 6 cm.

*Flower depth* (*height*).—About 3 cm.

*Flower longevity on plant*.—About 30 days.

*Flower longevity as a cut flower*.—About twelve days; flowers persistent.

*Fragrance*.—None detected.

*Flower buds*.—Shape: Ovoid. Length: About 3 cm. Diameter: About 2 cm. Color: Close to 144A.

*Petals*.—Quantity: Numerous; about 38 per flower. Length: About 3.1 cm. Width: About 3.3 cm. Shape: Nearly round. Apex: Acute. Base: Obtuse. Margin: Entire; slightly sinnuate. Texture, upper and lower surfaces: Smooth, glabrous. Color: When opening, upper surface: Close to 1D; towards the margin, close to 29D. When opening, lower surface: Close to 2D; towards the margin, close to 36A. Fully opened, upper surface: Close to 36C to 36D; towards the base, close to 150D. Older petals, close to 27D; towards the base, close to 150D. Fully opened, lower surface: Close to 36C to 36D; towards the base, close to 2D. Older petals, close to 144D tinged with close to 36D; towards the base, close to 2D.

*Sepals*.—Quantity per flower: Typically five. Length: About 3 cm. Width: About 9 mm. Shape: Roughly deltoid. Apex: Tapered. Base: Truncate. Margin: Entire; ciliate. Texture, upper and lower surfaces: Pubescent; leathery. Color: When opening, upper surface: Close to 143C; towards the center, close to 166B. When opening, lower surface: Close to 144A. Fully opened, upper surface: Close to 146B. Fully opened, lower surface: Close to 143A.

*Pedicels*.—Length: About 3.7 cm. Diameter: About 5.5 mm. Strength: Strong. Texture: Smooth, glabrous. Color: Close to 146A.

*Reproductive organs*.—Stamens: Quantity: About 110 per flower. Anther length: About 3 mm. Anther shape: Reniform. Anther color: Close to 164B. Filament color: Close to 1B. Pollen amount: Abundant. Pollen color: Close to 163A. Pistils: Quantity: About 90 per flower. Pistil length: About 1.4 cm. Stigma shape: Broadly reniform. Stigma color: Close to 162C. Style length: About 1 cm. Style color: Close to 160B. Receptacle height: About 1 cm. Receptacle diameter: About 8 mm. Receptacle shape: Cup-shaped. Receptacle texture: Smooth, glabrous. Receptacle color: Close to 144A. Seeds/fruits: Seed and fruit development have not been observed on plants of the new Rose.

Pathogen/pest resistance: Plants of the new Rose have not been observed to be resistant to pathogens and pests common to Roses.

Temperature tolerance: Plants of the new Rose have been observed to tolerate temperatures ranging from 0° C. to 35° C.

It is claimed:

1. A new and distinct Rose plant named 'Esm Durazno' as illustrated and described.

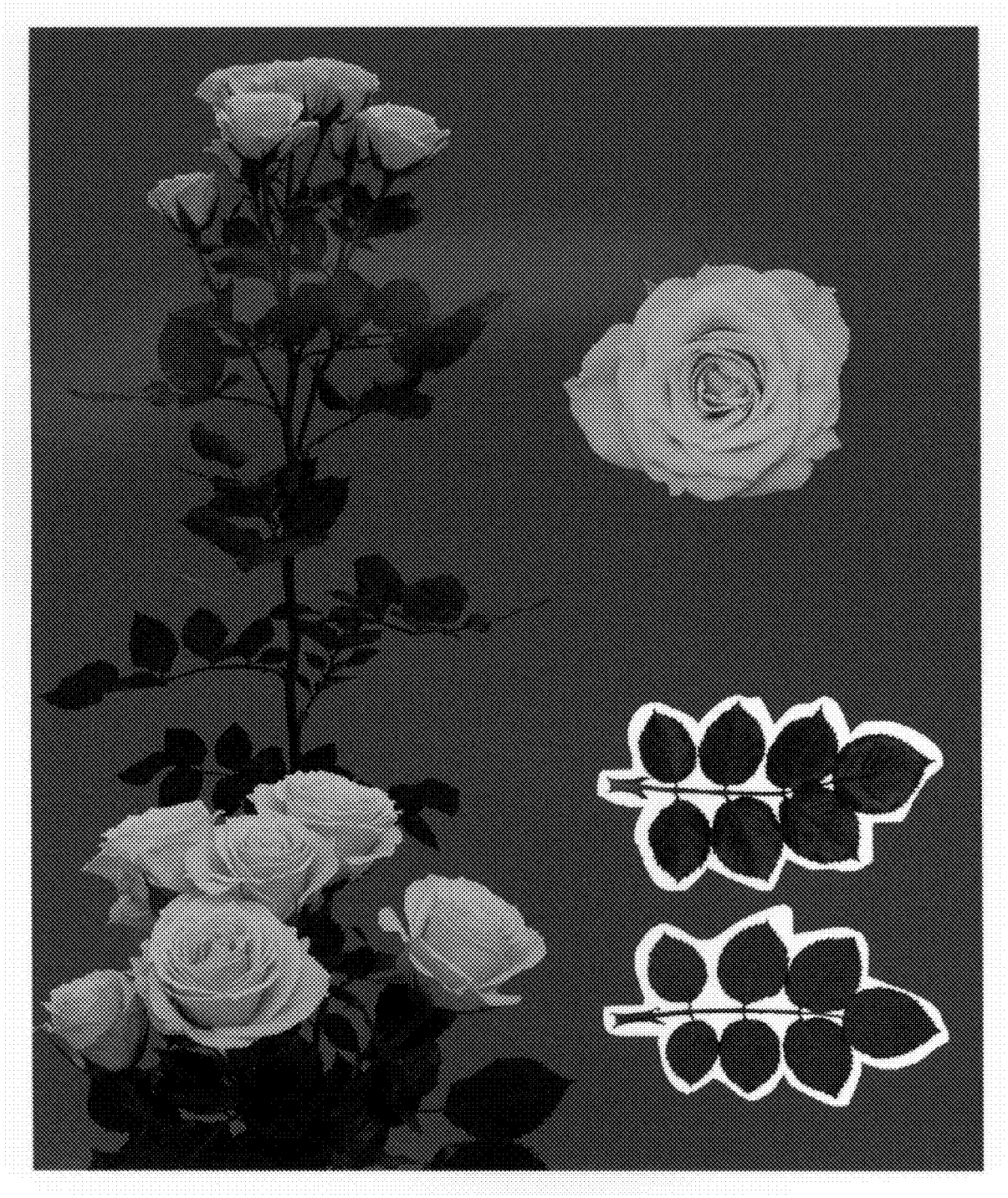

* * * * *